US012778520B2

(12) United States Patent
Yamakawa

(10) Patent No.: US 12,778,520 B2
(45) Date of Patent: Nov. 3, 2026

(54) DISPLAY DATA GENERATION APPARATUS, DISPLAY DATA GENERATION METHOD, AND NON-TRANSITORY COMPUTER READABLE STORAGE MEDIUM

(71) Applicant: Nihon Kohden Corporation, Tokyo (JP)

(72) Inventor: Daichi Yamakawa, Tokorozawa (JP)

(73) Assignee: Nihon Kohden Corporation, Tokyo (JP)

( * ) Notice: Subject to any disclaimer, the term of this patent is extended or adjusted under 35 U.S.C. 154(b) by 210 days.

(21) Appl. No.: 18/397,933

(22) Filed: Dec. 27, 2023

(65) Prior Publication Data

US 2024/0215928 A1 Jul. 4, 2024

(30) Foreign Application Priority Data

Dec. 28, 2022 (JP) ................................ 2022-211971

(51) Int. Cl.
*A61B 5/00* (2006.01)

(52) U.S. Cl.
CPC ............ *A61B 5/7425* (2013.01); *A61B 5/743* (2013.01); *A61B 5/7475* (2013.01)

(58) Field of Classification Search
CPC ....... A61B 5/7425; A61B 5/743; A61B 5/742; A61B 5/7475
See application file for complete search history.

(56) References Cited

U.S. PATENT DOCUMENTS

2014/0218368 A1 8/2014 Hatano et al.
2016/0253467 A1 9/2016 Kitagawa et al.
2019/0029610 A1* 1/2019 Utsunomiya .......... A61B 5/743
2019/0110759 A1 4/2019 Tanishima et al.
(Continued)

FOREIGN PATENT DOCUMENTS

JP 2014150845 A 8/2014
JP 2016162131 A 9/2016
(Continued)

OTHER PUBLICATIONS

Office Action issued in Japanese Patent Application No. 2022-211971, mailed on Jan. 27, 2026, 7 pages including 4 pages of machine English translation,.

*Primary Examiner* — Kee M Tung
*Assistant Examiner* — Thang Gia Huynh
(74) *Attorney, Agent, or Firm* — Dorsey & Whitney LLP

(57) ABSTRACT

A display data generation apparatus includes an input interface configured to receive vital signs information on a subject, one or more processors, and one or more memories configured to store at least one instruction to be executed by the processor. In a case where the at least one instruction is executed by the processor, the display data generation apparatus generates display data. The display data includes, among the vital signs information received by the input interface a first vital signs information that is used in a determination method for determining a condition of the subject, the first vital signs information being displayed in a first area, and a second vital signs information that is not used in the determination method, the second vital signs information being displayed in a second area different from the first area.

13 Claims, 9 Drawing Sheets

(56) References Cited

U.S. PATENT DOCUMENTS

| | | | |
|---|---|---|---|
| 2019/0189280 A1 | 6/2019 | Nagashima et al. | |
| 2019/0259499 A1 | 8/2019 | Hong et al. | |
| 2019/0307405 A1 | 10/2019 | Terry et al. | |
| 2019/0336085 A1* | 11/2019 | Kayser .................. | A61B 5/202 |
| 2020/0066415 A1 | 2/2020 | Hettig et al. | |
| 2021/0315529 A1 | 10/2021 | Wang et al. | |

FOREIGN PATENT DOCUMENTS

| | | |
|---|---|---|
| JP | 2019024943 A | 2/2019 |
| JP | 2019072473 A | 5/2019 |
| JP | 2019109818 A | 7/2019 |
| JP | 2019537130 A | 12/2019 |
| JP | 2020129396 A | 8/2020 |
| JP | 2021121368 A | 8/2021 |

* cited by examiner

*FIG. 2*

| VITAL SIGNS INFORMATION | SCORES | |
|---|---|---|
| | 0 | 1 |
| RESPIRATORY RATE | < 22 BREATHS/min | ≥ 22 BREATHS/min |
| SYSTOLIC BLOOD PRESSURE | > 100 mmHg | ≤ 100 mmHg |
| CONSCIOUSNESS | YES | NO |

FIG. 3

| VITAL SIGNS INFORMATION | SCORES | | | | | | |
|---|---|---|---|---|---|---|---|
| | 3 | 2 | 1 | 0 | 1 | 2 | 3 |
| RESPIRATORY RATE | ≤ 8 BREATHS/min | | 9 BREATHS/min TO 11 BREATHS/min | 12 BREATHS/min TO 20 BREATHS/min | | 21 BREATHS/min TO 24 BREATHS/min | ≥ 25 BREATHS/min |
| $SpO_2$ | ≤ 91% | 92% TO 93% | 94% TO 95% | ≥ 96% | | | |
| OXYGEN SUPPORT | | YES | | NO | | | |
| BODY TEMPERATURE | ≤ 35.0°C | | 35.1°C TO 36.0°C | 36.1°C TO 38.0°C | 38.1°C TO 39.0°C | ≥39.1°C | |
| SYSTOLIC BLOOD PRESSURE | ≤ 90 mmHg | 91 mmHg TO 100 mmHg | 101 mmHg TO 110 mmHg | 111 mmHg TO 219 mmHg | | | ≥ 220 mmHg |
| HEART RATE | ≤ 40 BEATS/min | | 41 BEATS/min TO 50 BEATS/min | 51 BEATS/min TO 90 BEATS/min | 91 BEATS/min TO 110 BEATS/min | 111 BEATS/min TO 130 BEATS/min | ≥ 131 BEATS/min |
| CONSCIOUSNESS | | | | CONSCIOUS | | | UNCONSCIOUS |

(CONT.)

(FIG. 4 CONTINUED)
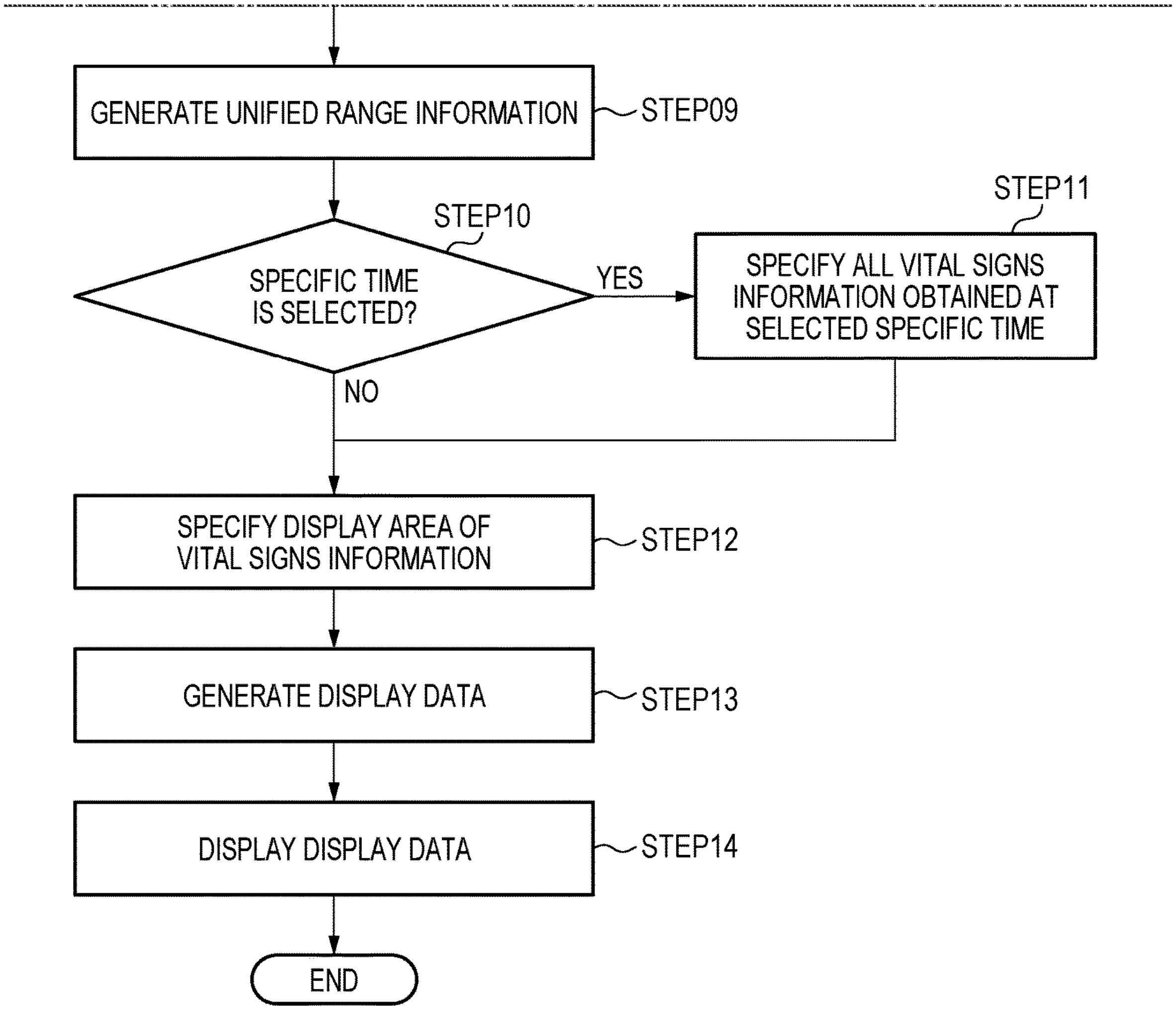

DISPLAY DATA GENERATION APPARATUS, DISPLAY DATA GENERATION METHOD, AND NON-TRANSITORY COMPUTER READABLE STORAGE MEDIUM

CROSS-REFERENCE TO RELATED APPLICATIONS

This application is based on and claims priority under 35 USC 119 from Japanese Patent Application No. 2022-211971 filed on Dec. 28, 2022, the entire content of which is incorporated herein by reference.

TECHNICAL FIELD

The presently disclosed subject matter relates to a display data generation apparatus, a display data generation method, and a non-transitory computer readable storage medium.

BACKGROUND ART

JP2021-121368A discloses a patient monitor configured to display, among trend graphs of alarm setting values related to a plurality of pieces of vital signs information, a trend graph of an alarm setting value related to vital signs information selected by a user on the same screen as a trend graph of vital signs information.

As a method for determining a condition of a subject, for example, a determination method such as national early warning score (NEWS) is known. When the condition of the subject is determined by using such a determination method, condition information based on the determination method and vital signs information used for the used determination method may be displayed on a patient monitor or the like. However, when it is desired to evaluate the condition of the subject more comprehensively and/or more specifically, not only the vital signs information used for the used determination method may be confirmed, but also other vital signs information not used for the determination method may be confirmed. As described above, when the condition of the subject is determined by using the determination method such as NEWS, there is a need to confirm not only the vital signs information necessary for performing the determination method but also the vital signs information which is unnecessary.

SUMMARY OF INVENTION

Aspect of non-limiting embodiments of the present disclosure relates to provide a display data generation apparatus, a display data generation method, and a non-transitory computer readable storage medium storing a computer program that are capable of displaying not only vital signs information used for a determination method for determining a condition of a subject but also vital signs information not used for the determination method.

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided:

1. A display data generation apparatus including:
   - an input interface configured to receive vital signs information on a subject;
   - one or more processors; and
   - one or more memories configured to store at least one instruction to be executed by the processor,
   - in which, in a case where the at least one instruction is executed by the processor, the display data generation apparatus generates display data, and
   - in which the display data includes, among the vital signs information received by the input interface:
     - a first vital signs information that is used in a determination method for determining a condition of the subject, the first vital signs information being displayed in a first area; and
     - a second vital signs information that is not used in the determination method, the second vital signs information being displayed in a second area different from the first area.

A display data generation method executed by a display data generation apparatus, the display data generation method including:

- generating display data, the display data including, among vital signs information on a subject:
  - a first vital signs information that is used in a determination method for determining a condition of the subject, the first vital signs information being displayed in a first area; and
  - a second vital signs information that is not used for the determination method, the second vital signs information being displayed in a second area different from the first area.

A non-transitory computer readable storage medium storing a computer program including instructions which, when executed by one or more processors provided in a display data generation apparatus, cause the display data generation apparatus to:

- generate display data, the display data including, among vital signs information on a subject:
  - a first vital signs information that is used for a determination method for determining a condition of the subject, the first vital signs information being displayed in a first area; and
  - a second vital signs information that is not used for the determination method, the second vital signs information being displayed in a second area different from the first area.

BRIEF DESCRIPTION OF DRAWINGS

Exemplary embodiment(s) of the present invention will be described in detail based on the following figures, wherein:

FIG. 2 illustrates reference values of qSOFA that is one of determination methods;

FIG. 3 illustrates reference values of NEWS that is one of determination methods;

DESCRIPTION OF EMBODIMENTS

Hereinafter, an example of an embodiment of the presently disclosed subject matter will be described with reference to the drawings. In the description of the present embodiment, a "left-right direction" and an "up-down direction" may be appropriately referred to for convenience of description. These directions are relative directions set for a display 42 of a user terminal device 40 illustrated in FIGS. 5 to 8. Here, the "left-right direction" can include a "leftward direction" and a "rightward direction". The "up-down direction" can include an "upward direction" and a "downward direction". In each of the drawings, a reference sign U indicates the upward direction. A reference sign D indicates the downward direction. A reference sign L indicates the leftward direction. A reference sign R indicates the rightward direction.

Figure 1:
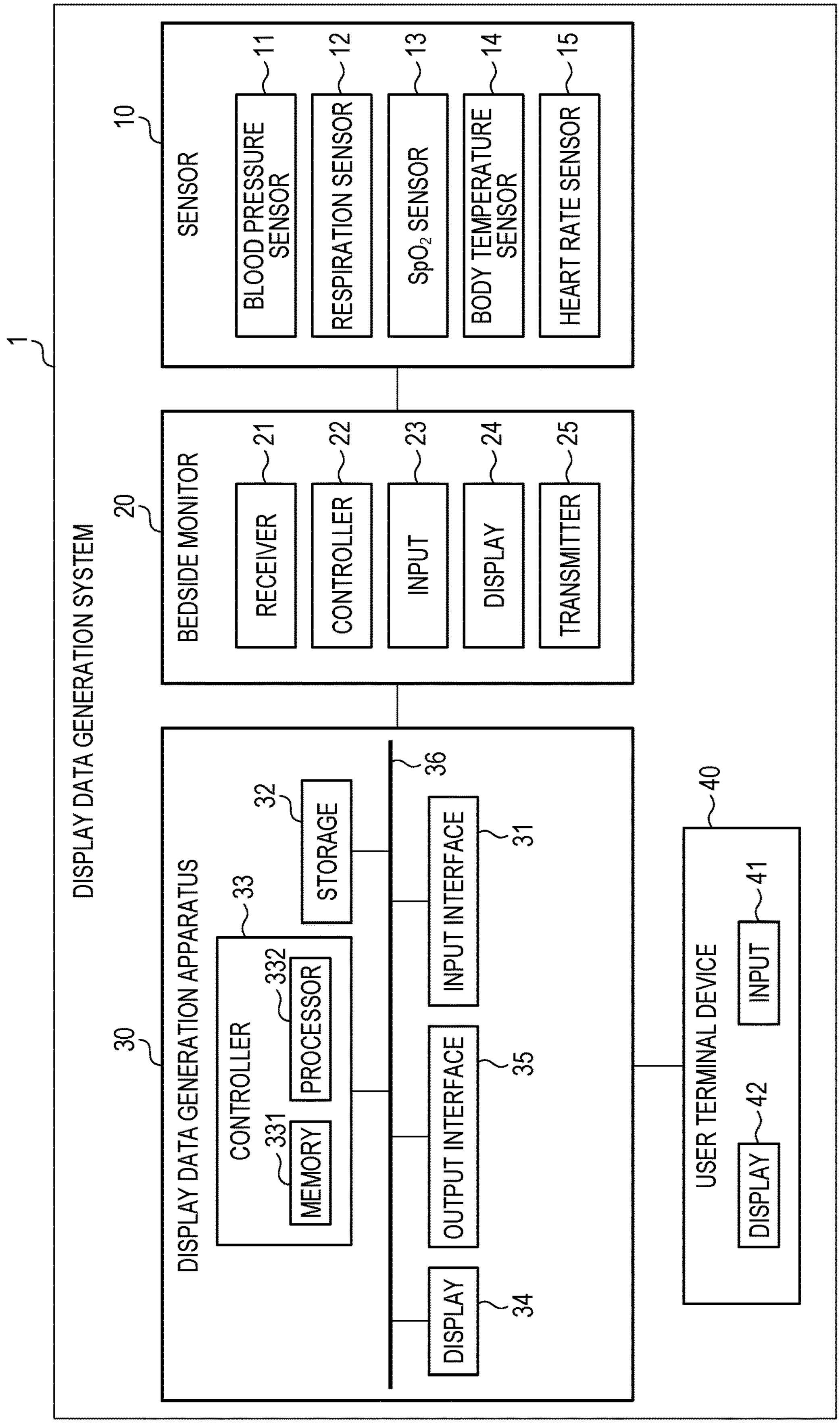
FIG. 1 is a block diagram of a display data generation system according to an embodiment of the presently disclosed subject matter.

First, a display data generation system 1 according to the present embodiment will be described with reference to FIG. 1. The display data generation system 1 is used in a medical facility such as a hospital. As illustrated in FIG. 1, the display data generation system 1 can include a sensor 10, a bedside monitor 20, a display data generation apparatus 30, and the user terminal device 40.

The sensor 10 can include a blood pressure sensor 11, a respiration sensor 12, an SpO2 sensor 13, a body temperature sensor 14, and a heart rate sensor 15. The sensor 10 may further include another sensor different from these sensors. The blood pressure sensor 11 is configured to obtain a blood pressure signal (an example of a vital signs signal) indicating a change over time in blood pressure (a systolic blood pressure, a diastolic blood pressure, and a mean blood pressure) of a subject. The blood pressure sensor 11 is, for example, a blood pressure monitor or a catheter configured to obtain an invasive blood pressure value. The respiration sensor 12 is configured to obtain a respiratory signal (an example of a vital signs signal) such as a respiratory rate indicating a respiratory state of the subject. The respiration sensor 12 is, for example, an electrode configured to obtain an impedance respiratory rate. The SpO2 sensor 13 is configured to obtain an SpO2 signal (an example of a vital signs signal) indicating a percutaneous arterial oxygen saturation (SpO2) of the subject. The SpO2 sensor 13 is, for example, a probe configured to obtains SpO2. The body temperature sensor 14 is configured to obtain a body temperature signal (an example of a vital signs signal) indicating a body temperature of the subject. The body temperature sensor 14 is a body temperature meter configured to measure the body temperature of the subject, a body temperature probe connected to the body temperature meter, or the like. The heart rate sensor 15 is configured to obtain a heart rate signal (an example of a vital signs signal) indicating a heart rate of the subject. The heart rate sensor 15 is, for example, an electrode configured to obtain a heart rate. In the present embodiment, the sensor 10 is configured to obtain a vital signs signal by a passive method, but may be configured to obtain a vital signs signal by an active method. In the measurement of the vital signs signal by the passive method, the vital signs signal is measured by receiving a signal from an object, without transmitting a signal such as light or an electromagnetic wave from the sensor 10 to the object. In the measurement of the vital signs signal by the active method, the vital signs signal information is measured by transmitting a signal from the sensor 10 to the object and by receiving a signal reflected by or transmitted through the object.

The bedside monitor 20 is disposed, for example, in a vicinity of the subject wearing the sensor 10. The bedside monitor 20 is electrically connected, in a wired or wireless manner, to the sensor 10 and the display data generation apparatus 30. The bedside monitor 20 can include a receiver 21, a controller 22, an input 23, a display 24, and a transmitter 25.

The receiver 21 is configured to receive various vital signs signals obtained by the sensor 10. The receiver 21 is configured to transmit the received various vital signs signals to the controller 22.

The controller 22 can include a memory and a processor, as a hardware configuration. For example, the memory can include a read only memory (ROM) configured to store various computer programs, and a random access memory (RAM) having a plurality of work areas in which various computer programs to be executed by the processors are stored. The processor is, for example, a central processing unit (CPU). The processor is configured to load, to the RAM, a computer program specified from various computer programs incorporated in the ROM, and configured to execute various processes in cooperation with the RAM. For example, the controller 22 is configured to generate various pieces of vital signs information based on various vital signs signals by executing computer programs by the processor in cooperation with the RAM. Examples of the vital signs information can include blood pressure information based on the blood pressure signal, respiratory information based on the respiratory signal, SpO2 information based on the SpO2 signal, body temperature information based on the body temperature signal, and heart rate information based on the heart rate signal. The controller 22 is configured to transmit various pieces of vital signs information to the input 23.

The input 23 is configured to receive an input operation performed by a user such as a medical worker. The user is a medical worker such as a doctor or a nurse. The input 23 is, for example, a touch panel superimposed on the display 24 or an operation button attached to a case. The user inputs, for example, consciousness information (an example of vital signs information) related to a consciousness of the subject and oxygen support information (an example of vital signs information) related to the necessity of oxygen support to the input 23. For example, in a case where the user confirms that the subject is not conscious, the user inputs consciousness information indicating that the subject is not conscious to the input 23. For example, in a case where the user determines that it is necessary to perform oxygen support to the subject, the user inputs oxygen support information indicating that it is necessary to perform oxygen support to the subject to the input 23. In this way, the bedside monitor 20 is configured to obtain not only vital signs information based on a vital signs signal of the subject obtained by the sensor 10 but also vital signs information on the subject via the input 23.

The display 24 is, for example, a liquid crystal display. The display 24 is configured to display, for example, various pieces of vital signs information generated by the controller 22 and various pieces of vital signs information input to the input 23.

The transmitter 25 is configured to transmit, to the display data generation apparatus 30, the various pieces of vital signs information generated by the controller 22 and the various pieces of vital signs information input to the input 23.

The display data generation apparatus 30 can include an input interface 31, a storage 32, a controller 33, a display 34, and an output interface 35. These components are communicably connected to each other via a bus 36.

The input interface 31 is configured to receive various pieces of vital signs information transmitted from the bedside monitor 20. That is, the vital signs information on the subject is input to the input interface 31. The input interface 31 is configured to transmit, for example, the received vital signs information to the controller 33.

The storage 32 is a storage such as a hard disk drive (HDD), a solid state drive (SSD), or a flash memory. The storage 32 is configured to store, for example, reference information indicating a reference value or the like of vital signs information used for quick SOFA (qSOFA) illustrated in FIG. 2, and type information indicating a type of vital signs information used for qSOFA. The storage 32 is configured to store, for example, reference information indicating a reference value or the like of vital signs information used for national early warning score (NEWS) illustrated in FIG. 3, and type information indicating a type of vital signs information used for NEWS. NEWS and qSOFA are determination methods used to determine whether the subject has sepsis. That is, the storage 32 is configured to store determination methods for determining a condition of the subject.

As illustrated in FIG. 2, the vital signs information used for qSOFA can include the respiratory rate, the systolic blood pressure, and the consciousness. In a case where the respiratory rate of the subject per minute is 22 breaths or more, a score related to the respiratory rate is 1. On the other hand, in a case where the respiratory rate of the subject per minute is less than 22 breaths, the score related to the respiratory rate is 0. In a case where the systolic blood pressure of the subject is 100 mmHg or less, a score related to the systolic blood pressure is 1. On the other hand, in a case where the systolic blood pressure of the subject exceeds 100 mmHg, the score related to the systolic blood pressure is 0. In a case where the subject is not conscious, a score related to the consciousness is 1. On the other hand, in a case where the subject is conscious, the score related to the consciousness is 0. These scores are summed up, and in a case where the summed score is 2 or more, there is a high probability that the subject has sepsis (that is, the condition of the subject is poor). In the present embodiment, regarding the vital signs information illustrated in FIG. 2, a range in which the score is 0 is assumed to be a normal range of the vital signs information used for qSOFA, and a range other than the normal range (a range in which the score is 1) is assumed to be an abnormal range of the vital signs information used for qSOFA. In the present embodiment, a range in which the respiratory rate per minute of the subject is 0 breaths or more and less than 22 breaths is assumed to be a normal range of the respiratory information (the respiratory rate) in qSOFA, and a range in which the respiratory rate per minute of the subject is 22 breaths or more is assumed to be an abnormal range of the respiratory information in qSOFA. A range in which the systolic blood pressure of the subject is more than 100 mmHg and 300 mmHg or less is assumed to be a normal range of the blood pressure information (the systolic blood pressure) in qSOFA, and a range in which the systolic blood pressure of the subject is 100 mmHg or less is assumed to be an abnormal range of the blood pressure information in qSOFA. An upper limit value set in the normal range of the blood pressure information (the systolic blood pressure) is, for example, a maximum value of the systolic blood pressure obtained from the subject or a value freely set by the user. Regarding the consciousness, it is assumed that the consciousness is digitized as 3 and unconsciousness is digitized as 1, a normal range of the consciousness information in qSOFA is 2 or more and 4 or less, and an abnormal range of the consciousness information in qSOFA is 0 or more and less than 2.

As illustrated in FIG. 3, the vital signs information used for NEWS can include the respiratory rate, the percutaneous arterial oxygen saturation (SpO2), the oxygen support, the body temperature, the systolic blood pressure, the heart rate, and the consciousness. For example, in a case where the respiratory rate of the subject per minute is 8 breaths or less, or 25 breaths or more, a score related to the respiratory rate is 3. In a case where the respiratory rate is 21 breaths or more and 24 breaths or less, the score related to the respiratory rate is 2. In a case where the respiratory rate is 9 breaths or more and 11 breaths or less, the score related to the respiratory rate is 1. In a case where the respiratory rate is 12 breaths or more and 20 breaths or less, the score related to the respiratory rate is 0. For example, in a case where the subject is not conscious, a score related to the consciousness is 3. On the other hand, in a case where the subject is conscious, the score related to the consciousness is 0. For the remaining parameters, a score is calculated based on a reference value or the like determined by a medical guideline or the like. These calculated scores are summed up. In a case where the added score is 5 or more, or in a case where there is one or more pieces of vital signs information having a score of 3 or more, there is a high probability that the subject has sepsis (that is, the condition of the subject is poor). In the present embodiment, regarding the vital signs information illustrated in FIG. 3, a range in which the score is 0 is assumed to be a normal range of the vital signs information used for NEWS, and a range other than the normal range (a range in which the score is 1 to 3) is assumed to be an abnormal range of the vital signs information used for NEWS. For example, a range in which the respiratory rate of the subject per minute is 12 breaths or more and 20 breaths or less is a normal range of the respiratory information (the respiratory rate) in NEWS, and a range in which the respiratory rate of the subject per minute is 11 breaths or less or 21 breaths or more is an abnormal range of the respiratory information in NEWS. In the present embodiment, it is assumed that a range in which the percutaneous arterial oxygen saturation of the subject is 96% or more and 100% or less is a normal range of the SpO2 information in NEWS, and a range in which the percutaneous arterial oxygen saturation of the subject is less than 96% is an abnormal range of the respiratory information in NEWS. Regarding the consciousness, it is assumed that the consciousness is digitized as 3 and the unconsciousness is digitized as 1, a normal range of the consciousness information in NEWS is 2 or more and 4 or less, and an abnormal range of the consciousness information in NEWS is 0 or more and less than 2. Regarding the oxygen support, it is assumed that a presence of oxygen support is digitized as 1, an absence of oxygen support is digitized as 3, a normal range of the oxygen support information in NEWS is 2 or more and 4 or less, and an abnormal range of the oxygen support information in NEWS is 0 or more and less than 2.

Description is referred back to FIG. 1, and the storage 32 will be described. The storage 32 is configured to store various types of information such as normal range information indicating a normal range of the vital signs information set for each piece of vital signs information, abnormal range information indicating an abnormal range of the vital signs information set for each piece of vital signs information, and candidate determination method information indicating a determination method that is selectable but not used. For example, the storage 32 is configured to transmit, to the controller 33, the normal range information and the abnormal range information, based on a control signal from the controller 33.

The controller 33 can include a memory 331 and a processor 332, as a hardware configuration. For example, the memory 331 can include a read only memory (ROM) configured to store various computer programs, and a random access memory (RAM) having a plurality of work areas in which various computer programs to be executed by the processor are stored. The processor 332 is, for example, a central processing unit (CPU). The processor 332 is configured to load, to the RAM, a computer program specified from various computer programs incorporated in the ROM, and is configured to execute various processes in cooperation with the RAM. For example, the controller 33 implements various processes by executing computer programs by the processor 332 in cooperation with the RAM.

The controller 33 is configured to generate condition information indicating the condition of the subject, based on the vital signs information received from the input interface 31 and the determination method stored in the storage 32. In a case where the condition information is generated, the controller 33 generates background information indicating a background corresponding to the condition of the subject. The controller 33 is configured to generate display data including the vital signs information received from the input interface 31 and the background information. The display data may include not only the vital signs information and the background information but also other information such as the normal range information, the abnormal range information, the condition information, the determination method information indicating a used determination method, the candidate determination method information, and identification information described later. In the display data, the background information is displayed to overlap with the vital signs information. On the other hand, the condition information is displayed not to overlap with the vital signs information. The display data can include a first area in which vital signs information used for a determination method for determining the condition of the subject is displayed, a second area in which vital signs information not used for the determination method is displayed, and a third area in which vital signs information obtained at a specific time is displayed.

The controller 33 is configured to control a color tone related to a display mode of the background information to be different from a color tone related to a display mode of the vital signs information. In the present embodiment, a color related to the display mode of the background information is lighter than a color related to the display mode of the vital signs information. For example, the controller 33 is configured to control the color related to the display mode of the background information to be lighter than the color related to the display mode of the vital signs information, by controlling the brightness and the chroma related to the display mode of the background information to be lower than the brightness and the chroma related to the display mode of the vital signs information. For example, the controller 33 is configured to control the color related to the display mode of the background information to be lighter than the color related to the display mode of the vital signs information, by controlling the brightness related to the display mode of the background information to be lower than the brightness related to the display mode of the vital signs information. For example, the controller 33 is configured to control the color related to the display mode of the background information to be lighter than the color related to the display mode of the vital signs information, by controlling the chroma related to the display mode of the background information to be lower than the chroma related to the display mode of the vital signs information. In the present embodiment, the color tone is determined by controlling RGB gradient by the controller 33. Here, the brightness can be obtained based on a maximum value of RGB, and the chroma is obtained based on a value obtained by dividing, by the maximum value of RGB, a value obtained by subtracting a minimum value of RGB from the maximum value of RGB. Accordingly, the brightness related to the display mode of the background information being lower than the brightness related to the display mode of the vital signs information means that a maximum value of RGB related to the display mode of the background information is smaller than a maximum value of RGB related to the display mode of the vital signs information. The chroma related to the display mode of the background information being lower than the chroma related to the display mode of the vital signs information means that a value obtained by dividing, by the maximum value of RGB, a value obtained by subtracting a minimum value of RGB from the maximum value of RGB related to the display mode of the background information is smaller than a value obtained by dividing, by the maximum value of RGB, a value obtained by subtracting a minimum value of RGB from the maximum value of RGB related to the display mode of the vital signs information.

The controller 33 is configured to control a color tone related to a display mode of the condition information to be different from the color tone related to the display mode of the background information. In the present embodiment, the hue related to the display mode of the condition information corresponds to the hue related to the display mode of the background information. The expression "the hues correspond to each other" means that values obtained from the following formulas are the same. When a maximum value of RGB is MAX, a minimum value is MIN, and R is the maximum value, a hue $H=60\times((G-B)/(MAX-MIN))$. When G is the maximum value, the hue $H=60\times((B-R)/(MAX-MIN))+120$. When B is the maximum value, the hue $H=60\times((R-G)/(MAX-MIN))+240$. When RGB has the same value, the hue H is 0.

The color related to the display mode of the condition information is darker than the color related to the display mode of the background information. The color tone related to the display mode of the condition information and the color tone related to the display mode of the background information are also determined by controlling the RGB gradient by the controller 33 as described above.

The controller 33 is configured to generate a control signal for transmitting the normal range information and the abnormal range information corresponding to the vital signs information received from the input interface 31 to the controller 33, and is configured to transmit the control signal to the storage 32. The storage 32 is configured to transmit the normal range information and the abnormal range information corresponding to the vital signs information received from the input interface 31 to the controller 33, based on the control signal. In this manner, the controller 33 is configured to receive, from the storage 32, the normal range information and the abnormal range information corresponding to the vital signs information received from the input interface 31. The display data generated by the controller 33 may include the normal range information and the abnormal range information related to the vital signs information received from the input interface 31. In this case, the vital signs information is displayed to overlap with the background information and at least one of the normal range information or the abnormal range information. The controller 33 may be configured to generate the display data such that a color tone related to a display mode of the normal range information is different from a color tone related to a display mode of the abnormal range information. The color tone is also determined by controlling the RGB gradient by the controller 33, as described above.

The controller 33 is configured to classify the vital signs information input to the input interface 31 into vital signs information used for a determination method and vital signs information not used for the determination method, based on the determination method information and the type information. The controller 33 is configured to generate the identification information for identifying a determination method used and a determination method not used, based on the determination method information and the candidate determination method information.

In a case where a plurality of pieces of vital signs information are input to the input interface 31, the controller 33 is configured to generate unified range information indicating a unified range based on the normal range information and the abnormal range information corresponding to each piece of vital signs information. The unified range is a range for uniformly defining a normal range and an abnormal range of the plurality of pieces of vital signs information. The plurality of pieces of vital signs information input to the input interface 31 are collectively displayed in the unified range in the display data generated by the controller 33.

Computer programs may be stored in, for example, various types of non-transitory computer readable storage medium, and may be supplied to a computer. The non-transitory computer readable storage medium can include various types of tangible storage medium. Examples of the non-transitory computer readable medium can include a magnetic recording medium (for example, a flexible disk, a magnetic tape, or a hard disk drive), a magneto-optical recording medium (for example, a magneto-optical disk), a CD read only memory (ROM), a CD-R, a CD-R/W, and a semiconductor memory (for example, a mask ROM, a programmable ROM (PROM), an erasable PROM (EPROM), or a flash ROM).

The display 34 is a touch screen display such as a liquid crystal display or an organic EL display. The display 34 is configured to display, for example, the display data received from the controller 33.

The output interface 35 is configured to output the display data received from the controller 33 to the user terminal device 40. For example, the output interface 35 is configured to output an output signal OS corresponding to the display data to the user terminal device 40. The output interface 35 may include, as necessary, a circuit configured to convert output data into the output signal OS that can be processed by the user terminal device 40.

The user terminal device 40 is an electronic device such as a desktop PC, a notebook PC, a tablet terminal, or a smartphone. The user terminal device 40 can include an input 41 and the display 42.

The input 41 is configured to receive an input operation executed by a user such as a medical worker. The input 41 is, for example, a touch panel superimposed on the display 42 or an operation button attached to a case. To the input 41, the determination method information indicating a used determination method, selection time information indicating a specific time at which the user desires to confirm the vital signs information, and the like are input by the user. The input 41 is configured to transmit the determination method information, the selection time information, and the like input by the user to the display data generation apparatus 30.

The display 42 is, for example, a liquid crystal display. The display 42 is configured to display, for example, display data output from the output interface 35.

First Embodiment

Figure 4:
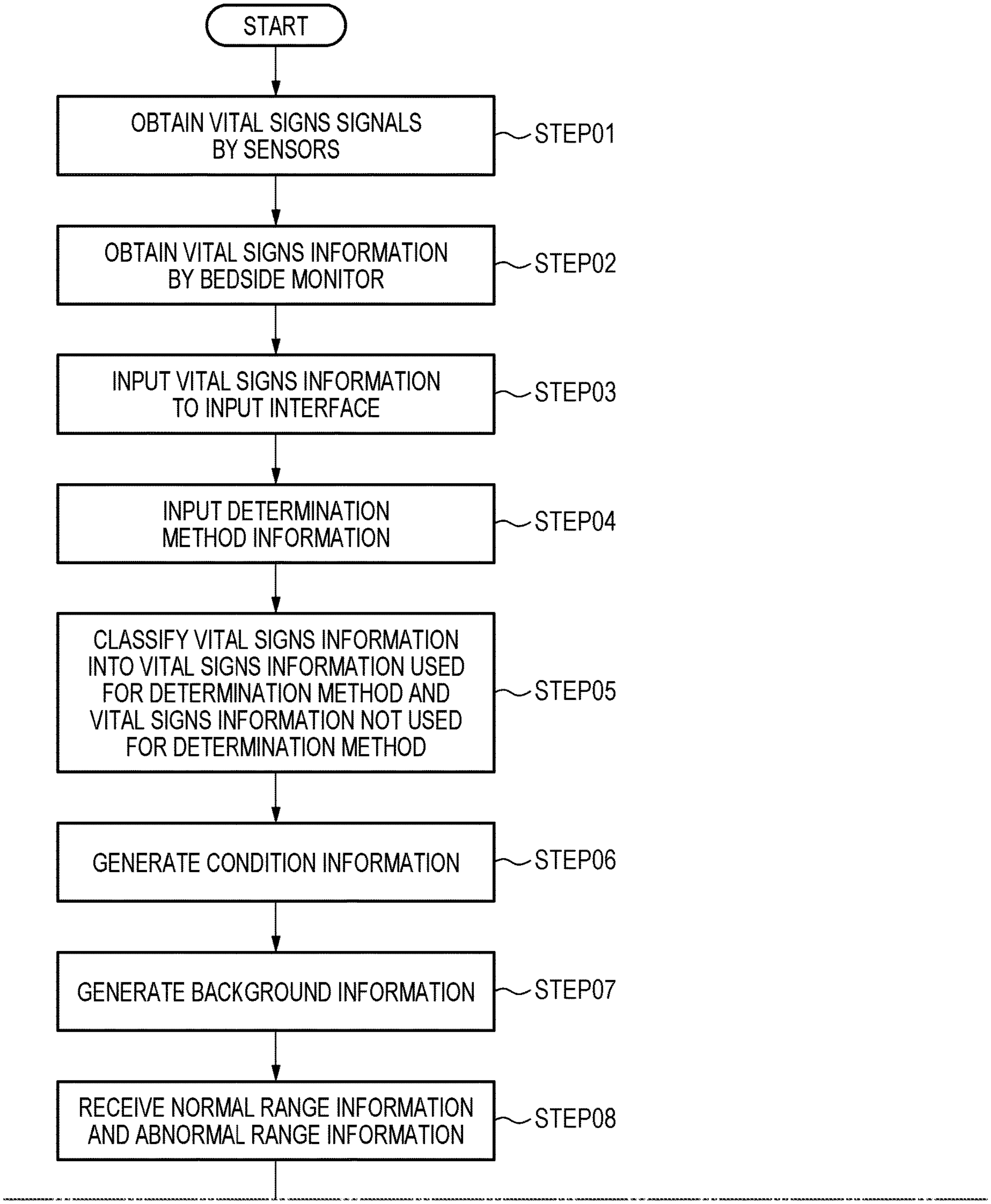
FIG. 4 is a flowchart of a display data generation method according to an embodiment of the presently disclosed subject matter.
Figure 5:
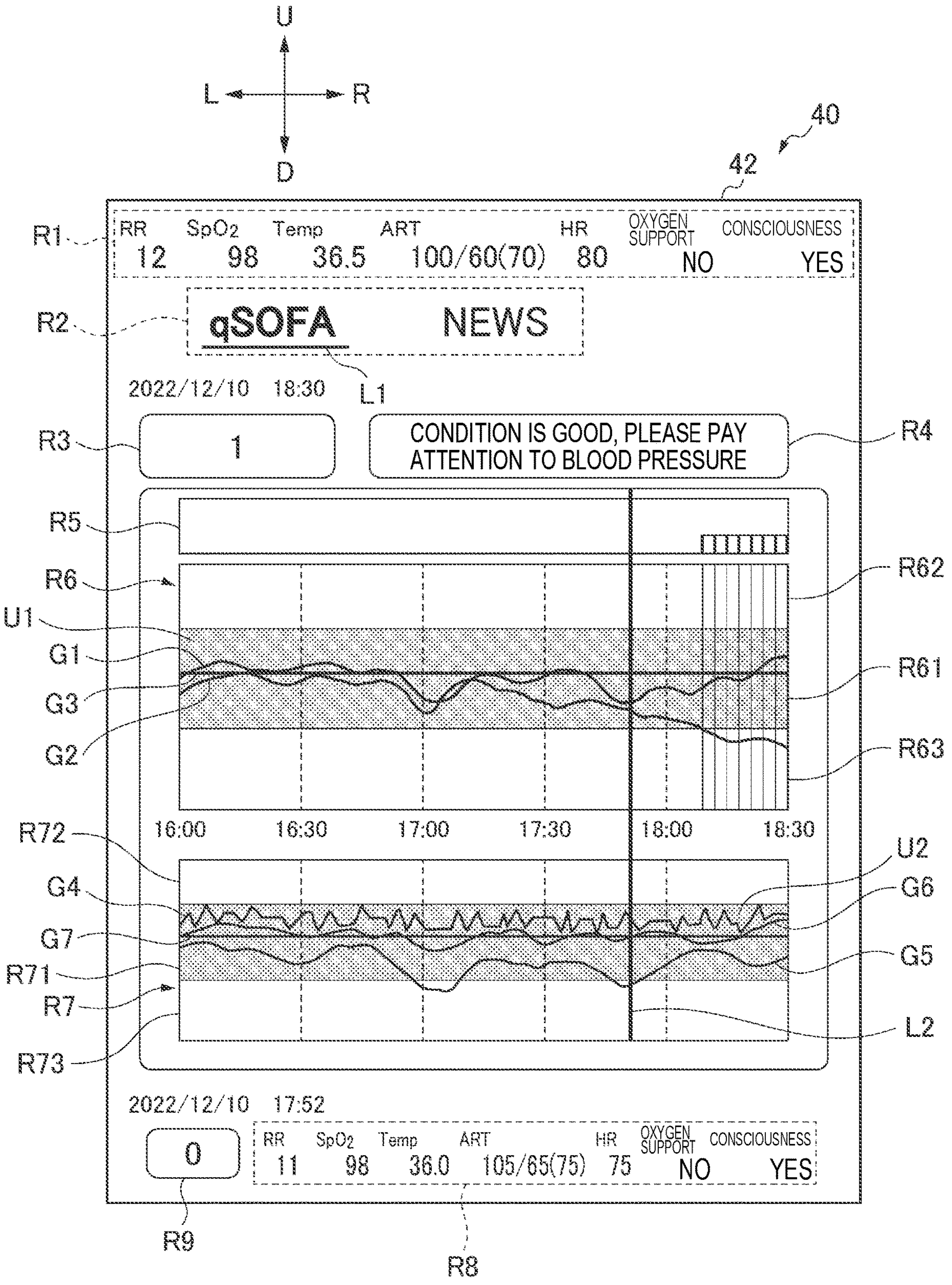
FIG. 5 illustrates an example of a screen on which display data is displayed.
Figure 6:
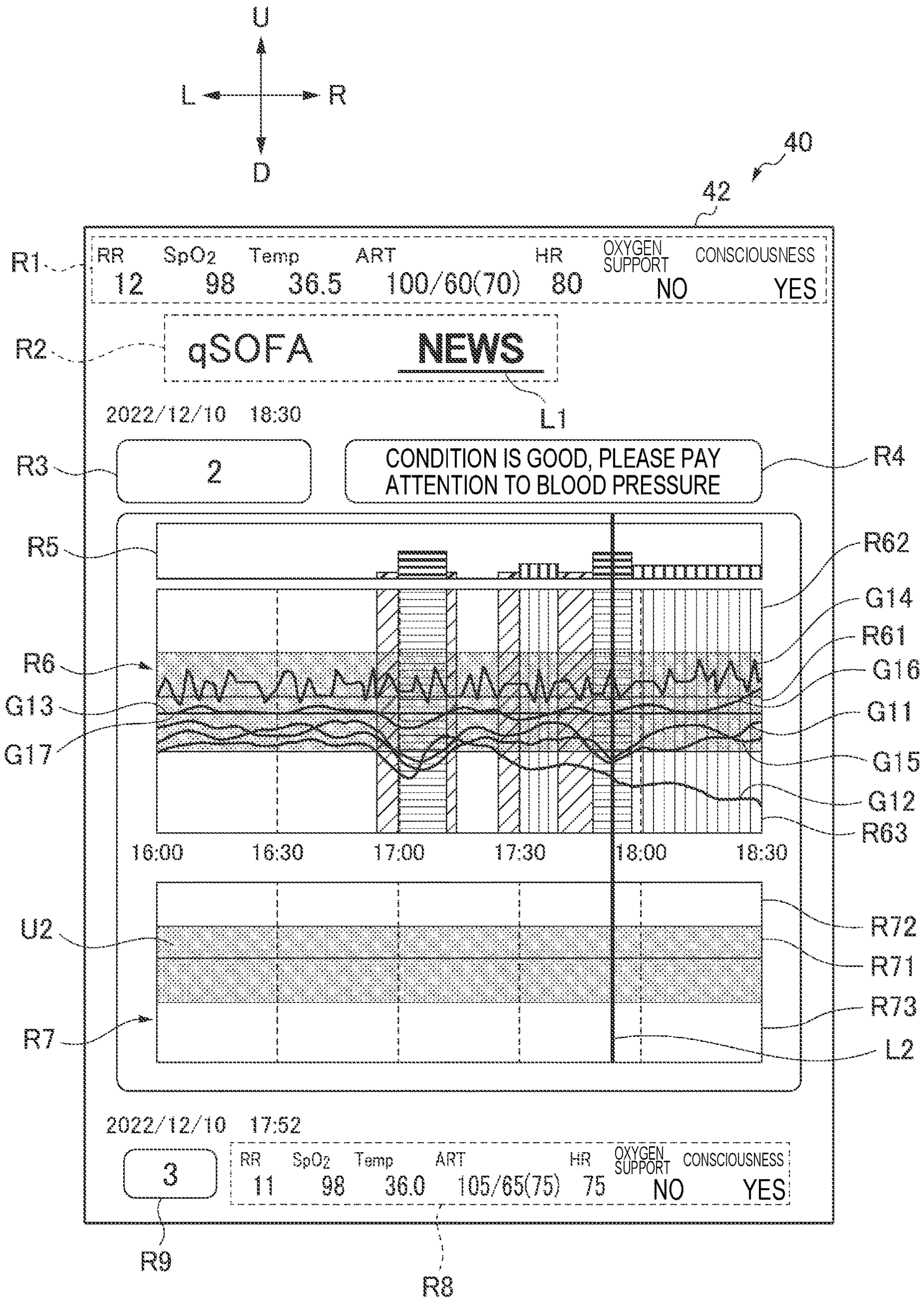
FIG. 6 illustrates an example of the screen on which display data is displayed.

Next, a display data generation method according to the present embodiment will be described with reference to FIGS. 4 to 6. FIG. 4 is a flowchart of the display data generation method according to the present embodiment. It is assumed that a current time in the present embodiment is 18:30, Dec. 10, 2022, and the display data generation method illustrated in FIG. 4 is executed at 18:30, Dec. 10, 2022. In the present embodiment, it is assumed that the vital signs information is obtained from 16:00, Dec. 10, 2022 to 18:30, Dec. 10, 2022. In the present embodiment, it is assumed that the selection time information, which indicates that the time at which the user desires to confirm the vital signs information is 17:52, Dec. 10, 2022, is input to the input 41 of the user terminal device 40. That is, the specific time selected by the user in the present embodiment is 17:52, Dec. 10, 2022.

In the present embodiment, the respiratory rate, the percutaneous arterial oxygen saturation, the body temperature, the systolic blood pressure, the diastolic blood pressure, the mean blood pressure, the heart rate, the oxygen support, the consciousness, scores based on qSOFA, and scores based on NEWS of the subject at 17:52 and 18:30, Dec. 10, 2022 are as illustrated in Table 1.

TABLE 1

| Time | Respiratory rate | Percutaneous arterial oxygen saturation | Body temperature | Systolic blood pressure | Diastolic blood pressure | Mean blood pressure |
|---|---|---|---|---|---|---|
| 17:52, Dec. 10, 2022 | 11 Breaths/min | 98% | 36.0° C. | 105 mmHg | 65 mmHg | 75 mmHg |
| 18:30, Dec. 10, 2022 | 12 Breaths/min | 98% | 36.5° C. | 100 mmHg | 60 mmHg | 70 mmHg |

| Time | Heart rate | Oxygen support | Consciousness | Scores based on qSOFA | Scores based on NEWS |
|---|---|---|---|---|---|
| 17:52, Dec. 10, 2022 | 75 Beats/min | No | Yes | 0 | 3 |
| 18:30, Dec. 10, 2022 | 80 Beats/min | No | Yes | 1 | 2 |

As illustrated in FIG. 4, vital signs signals of the subject are obtained by the sensor 10 (STEP 01). In the present embodiment, the sensor 10 is configured to obtain the respiratory signal, the SpO2 signal, the body temperature signal, the blood pressure signal, and the heart rate signal. The various pieces of vital signs signals obtained by the sensor 10 are transmitted to the receiver 21 of the bedside monitor 20.

The bedside monitor 20 obtains the various pieces of vital signs information (STEP 02). In the present embodiment, the user inputs the oxygen support information and the consciousness information to the input 23. For this reason, the bedside monitor 20 is configured to obtain the respiratory information, the SpO2 information, the body temperature information, the blood pressure information, and the heart rate information generated by the controller 22, based on the respiratory signal, the SpO2 signal, the body temperature signal, the blood pressure signal, and the heart rate signal received via the receiver 21. The bedside monitor 20 is configured to obtain the oxygen support information and the consciousness information, via the input 23. The transmitter 25 of the bedside monitor 20 is configured to transmit, to the input interface 31 of the display data generation apparatus 30, various pieces of vital signs information generated by the controller 22 and various pieces of vital signs information input to the input 23.

Various pieces of vital signs information transmitted from the transmitter 25 of the bedside monitor 20 are input to the input interface 31 (STEP 03). The input interface 31 is configured to transmit the input vital signs information to the controller 33.

The determination method information indicating a used determination method is input to the input 41 of the user terminal device 40 (STEP 04). For example, the user inputs, to the input 41 of the user terminal device 40, determination method information indicating that the used determination method is qSOFA. The input of the determination method information to the input 41 is performed, for example, by typing the used determination method on the touch panel superimposed on the display 42. The user terminal device 40 is configured to transmit, to the display data generation apparatus 30, the determination method information input to the input 41.

The controller 33 is configured to classify the vital signs information input to the input interface 31 into vital signs information used for the determination method and vital signs information not used for the determination method, based on the determination method information received from the user terminal device 40 and the type information stored in the storage 32 (STEP 05). In a case where the used determination method is qSOFA, for example, the vital signs information used for the determination method is the respiratory information, the blood pressure information, and the consciousness information, and the vital signs information not used for the determination method is the SpO2 information, the body temperature information, the heart rate information, and the oxygen support information. In STEP 05, the controller 33 generates the identification information, based on the determination method information and the candidate determination method information.

The controller 33 generates the condition information indicating the condition of the subject, based on the vital signs information received from the input interface 31 and the reference information stored in the storage 32 (STEP 06). In a case where the used determination method is qSOFA, the controller 33 generates the condition information, based on the respiratory information, the blood pressure information, and the consciousness information, and the reference information related to qSOFA. Here, as an example, a case in which the controller 33 generates the condition information indicating the condition of the subject at the current time will be described. In the present embodiment, the respiratory rate of the subject at the current time is 12 breaths. The systolic blood pressure of the subject at the current time is 100. At the current time, the subject is conscious. Accordingly, the controller 33 generates condition information indicating that the score based on qSOFA at the current time is 1.

The controller 33 generates the background information indicating the background corresponding to the condition of the subject determined based on the vital signs information used for the determination method used for determining the condition of the subject and the determination method (STEP 07). For example, in a case where the condition of the subject is determined based on qSOFA at the current time, the controller 33 generates the background information indicating the background corresponding to the score (that is, 1) based on qSOFA at the current time.

The controller 33 is configured to generate a control signal for transmitting the normal range information and the abnormal range information corresponding to the vital signs information received from the input interface 31 to the controller 33, and is configured to transmit the control signal to the storage 32. Accordingly, the controller 33 receives the normal range information and the abnormal range information corresponding to the vital signs information (STEP 08).

The controller 33 generates the unified range information indicating a unified range based on the normal range information and the abnormal range information corresponding to the vital signs information (STEP 09). In the present embodiment, the controller 33 is configured to generate the unified range information indicating the unified range based on the normal range information and the abnormal range information corresponding to the vital signs information used for the determination method, and the unified range information indicating the unified range based on the normal range information and the abnormal range information corresponding to the vital signs information not used for the determination method.

First, the unified range information indicating the unified range based on the normal range information and the abnormal range information corresponding to the vital signs information used for the determination method will be described. Here, it is assumed that qSOFA is used as the determination method. The normal range of the respiratory rate per minute corresponding to the respiratory information is 0 breaths or more and less than 22 breaths, and the abnormal range of the respiratory rate per minute corresponding to the respiratory information is 22 breaths or more. The normal range of the systolic blood pressure corresponding to the blood pressure information is more than 100 mmHg and 300 mmHg or less, and the abnormal range of the systolic blood pressure corresponding to the blood pressure information is 100 mmHg or less. The normal range of the consciousness corresponding to the consciousness information is 2 or more and 4 or less, and the abnormal range of the consciousness corresponding to the consciousness information is 0 or more and less than 2. The controller 33 is configured to generate the unified range information indicating the unified range based on the normal range information and the abnormal range information corresponding to the respiratory information, the blood pressure information, and the consciousness information. The controller 33 is configured to calculate a median value of an upper limit value and a lower limit value in the normal range of each piece of the vital signs information, configured to divide the upper limit value and the lower limit value in the normal range of each piece of the vital signs information by the median value corresponding to each piece of vital signs information, and configured to multiply values after the division by a largest median value to generate the unified range information. That is, the controller 33 is configured to correct normal ranges of the vital signs information, which are originally different numerical ranges, as described above, thereby matching display positions of the normal ranges of the vital signs information and setting the unified range. In the present embodiment, the median value of the upper limit value and the lower limit value in the normal range of the respiratory information is 11 breaths. The median value of the upper limit value and the lower limit value in the normal range of the blood pressure information is 200 mmHg. The median value of the upper limit value and the lower limit value in the normal range of the consciousness information is 3. The controller 33 multiplies the upper limit value and the lower limit value in the normal range of the respiratory information by 200/11 and multiplies the upper limit value and the lower limit value in the normal range of the consciousness information by 200/3 to generate the unified range information. At this time, the controller 33 multiplies the respiratory rate indicated by the obtained respiratory information by 200/11, and multiplies the numerical value corresponding to the obtained consciousness information by 200/3.

Next, the unified range information indicating the unified range based on the normal range information and the abnormal range information corresponding to the vital signs information not used for the determination method will be described. In a case where qSOFA is used in the present embodiment, the normal range of the vital signs information (the SpO2 information, the body temperature information, the heart rate information, and the oxygen support information) not used for qSOFA is in accordance with the normal range and the abnormal range of the vital signs information in NEWS. That is, for example, the normal range of the body temperature information is 36.1 degrees or more and 38.0 degrees or less, and the abnormal range of the body temperature information is 36.0 degrees or less or 38.1 degrees or more. According to the above-described principle, the controller 33 is configured to generate the unified range information indicating the unified range based on the normal range information and the abnormal range information corresponding to the SpO2 information, the body temperature information, the heart rate information, and the oxygen support information.

As illustrated in FIG. 4, the controller 33 determines whether a specific time at which the vital signs information is desired to be confirmed is selected (STEP 10). When selecting the specific time at which the user desires to check the vital signs information, the user inputs the selection time information indicating the specific time at which the user desires to confirm the vital signs information to the input 41 of the user terminal device 40. In a case where the selection time information is input to the input 41 of the user terminal device 40, the user terminal device 40 transmits the selection time information input to the input 41 to the display data generation apparatus 30. In a case where the display data generation apparatus 30 receives the selection time information from the user terminal device 40, the controller 33 determines that the specific time at which the vital signs information is desired to be confirmed is selected (YES in STEP 10), and performs STEP 11. On the other hand, in a case where the display data generation apparatus 30 does not receive the selection time information from the user terminal device 40, the controller 33 determines that no specific time at which the vital signs information is desired to be confirmed is selected (NO in STEP 10), and performs STEP 12. In the present embodiment, since 17:52, Dec. 10, 2022 is selected as the specific time at which the vital signs information is desired to be confirmed (YES in STEP 10), the controller 33 performs STEP 11.

The controller 33 specifies all the vital signs information obtained at the specific time selected by the user (STEP 11). Since the specific time selected by the user in the present embodiment is 17:52, Dec. 10, 2022, all the vital signs information (the respiratory information, the SpO2 information, the body temperature information, the blood pressure information, the heart rate information, the oxygen support information, and the consciousness information) obtained at 17:52, Dec. 10, 2022 is specified.

The controller 33 specifies a display area of the vital signs information (STEP 12). Specifically, the controller 33 specifies the first area as the display area of the vital signs information used for the determination method, the second area as the display area of the vital signs information not used for the determination method, and the third area as the display area of the vital signs information obtained at a specific time freely selected by the user. In a case where the used determination method is qSOFA, for example, the display area of the respiratory information, the blood pressure information, and the consciousness information obtained from 16:00, Dec. 10, 2022 to the current time is the first area. The display area of the SpO2 information, the body temperature information, the heart rate information, and the oxygen support information obtained from 16:00, Dec. 10, 2022 to the current time is the second area. The display area of the respiratory information, the SpO2 information, the body temperature information, the blood pressure information, the heart rate information, the oxygen support information, and the consciousness information obtained at 17:52, Dec. 10, 2022 is the third area.

The controller 33 generates display data including the vital signs information, the background information, the normal range information, the abnormal range information, the condition information, the determination method information, the candidate determination method information, and the identification information (STEP 13). The controller 33 transmits the generated display data to the display 34 and/or the output interface 35. In a case where the display data is transmitted to the output interface 35, the output interface 35 outputs the received display data to the user terminal device 40. In the present embodiment, the display data is transmitted to the output interface 35 and output to the user terminal device 40.

In a case where the display data is output to the user terminal device 40, the display data is displayed on the display 42 of the user terminal device 40 (STEP 14). At this time, the display data illustrated in FIG. 5 or FIG. 6 is displayed on the display 42 of the user terminal device 40. The display data illustrated in FIG. 5 is display data displayed on the display 42 when qSOFA is used. The display data illustrated in FIG. 6 is display data displayed on the display 42 when NEWS is used.

First, display data displayed on the display 42 when qSOFA is used as the determination method will be described. As illustrated in FIG. 5, the display data can include areas R1 to R9. The area R1 displays the vital signs information (the respiratory information, the SpO2 information, the body temperature information, the blood pressure information, the heart rate information, the oxygen support information, and the consciousness information) of the subject at the current time of 18:30, Dec. 10, 2022.

The area R2 below the area R1 displays a determination method for determining the condition of the subject. In the present embodiment, qSOFA and NEWS are displayed in the area R2. In the present embodiment, the used determination method is qSOFA, and thus qSOFA is the determination method indicated by the determination method information, and NEWS is the determination method indicated by the candidate determination method information. In a vicinity of characters of the used determination method indicated by the determination method information, the identification information for identifying the determination method used and the determination method not used is displayed. In the example illustrated in FIG. 5, qSOFA is used, and thus a straight line L1 is displayed in the vicinity of characters "qSOFA" as the identification information indicating that qSOFA is used. The straight line L1 is displayed below the characters "qSOFA".

The area R3 below the area R2 displays, as the condition information based on the used determination method at 18:30, Dec. 10, 2022, the score based on the used determination method. In the example illustrated in FIG. 5, the used determination method is qSOFA, and the score based on qSOFA at 18:30, Dec. 10, 2022 is 1, and thus "1" is displayed in the area R3.

The area R4 on a right side of the area R3 displays a message corresponding to a determination result of the controller 33 at the current time. In the example illustrated in FIG. 5, a message "condition is good, please pay attention to blood pressure" is displayed in the area R4. The information displayed in the area R4 is not limited to a message, and for example, a color or the like corresponding to the determination result of the controller 33 at the current time may be displayed.

The area R5 below the area R3 and the area R4 displays the condition information based on the used determination method in a period from 16:00, Dec. 10, 2022 to the current time in a form of bar graphs. In the example illustrated in FIG. 5, bar graphs corresponding to scores based on qSOFA in the period from 16:00, Dec. 10, 2022 to the current time are displayed in the area R5. In the present embodiment, in a case where the score of qSOFA is 1, the bar graph is colored in yellow, and in a case where the score based on qSOFA is 2 or more, the bar graph is colored in red. In FIG. 5, a bar graph hatched with vertical lines indicates a bar graph colored in yellow. The bar graphs are arranged in time series, and the left bar graphs represent the condition information before that of the right bar graphs in time.

The area R6 below the area R5 displays, among the vital signs information from 16:00, Dec. 10, 2022 to the current time, the vital signs information used for the used determination method (the determination method indicated by the determination method information) in a form of vital graphs extending on a timeline. Accordingly, the area R6 is an example of the first area. In the example illustrated in FIG. 5, the vital signs information (the respiratory information, the blood pressure information, and the consciousness information) used for qSOFA from 16:00, Dec. 10, 2022 to the current time is displayed in the area R6 in a form of vital graphs extending on the timeline. The vital graph indicating the respiratory information is a graph G1. The vital graph indicating the blood pressure information is a graph G2. The vital graph indicating the consciousness information is a graph G3. The graphs G1 to G3 do not overlap with the bar graphs of the condition information displayed in the area R5. Timelines in the area R5 and the area R6 coincide with each other, and the graphs G1 to G3 and the bar graphs of the condition information are displayed in correspondence with each other along the timelines.

In the area R6, the background information indicating the background according to the condition of the subject determined based on the vital signs information and the determination method overlaps with the graphs G1 to G3. That is, the background information overlaps with the vital signs information. The background information in the area R6 coincides with the timeline of the condition information in the area R5. The background corresponding to the background information at a certain time is colored in a color that has a hue corresponding to a hue of a color of the bar graph of the condition information at the same time, and that is lighter than the color of the bar graph. In other words, at least one of the brightness or the chroma related to the display mode of the condition information is higher than at least one of the brightness or the chroma related to the display mode of the background information. The present specification is not intended to compare the brightness related to the display mode of the condition information and the chroma related to the display mode of the background information, or the chroma related to the display mode of the condition information and the brightness related to the display mode of the background information. In the example illustrated in FIG. 5, the background information at the time when the score of qSOFA is 1 is colored in light yellow. For convenience of description, in FIG. 5, a thickness of the hatched line represents a height of the brightness and/or the chroma (that is, a color intensity) of the color. The thicker the hatched line is, the higher the brightness and/or the chroma of the color is (that is, the darker the color is). This also applies to the display data illustrated in FIGS. 6 and 7. In this manner, the color tone related to the display mode of the background information is different from the color tone related to the display mode of the condition information. In the present embodiment, the color related to the display mode of the background information is lighter than colors related to display modes of the graphs G1 to G3. In other words, at least one of the brightness or the chroma related to the display mode of the background information is lower than at least one of the brightness or the chroma related to the display modes of the graphs G1 to G3. The present specification is not intended to compare the brightness related to the display mode of the background information and the chroma related to the display mode of the graphs G1 to G3, or the chroma related to the display mode of the background information and the brightness related to the display mode of the graphs G1 to G3. For convenience of description, in FIG. 5, the thickness of the line represents the height of the brightness and/or the chroma (that is, the color intensity) of the color. The thicker the line is, the higher the brightness and/or the chroma of the color is (that is, the darker the color is). That is, the color tone related to the display mode of the background information is different from the color tone related to the display modes of the graphs G1 to G3.

The area R6 can include an area R61 corresponding to the normal range of the vital signs information used for the used determination method, and an area R62 and an area R63 corresponding to the abnormal range of the vital signs information used for the used determination method. In the example illustrated in FIG. 5, the normal range and the abnormal range of the vital signs information used for the used determination method are uniformly defined by a unified range U1 indicated by the unified range information generated by the controller 33 according to the above principle. Specifically, in the area R6, a plurality of pieces of vital signs information (graphs G1 to G3) are collectively displayed in the unified range U1. That is, in the area R6, display positions of the normal ranges of the vital signs information used for the used determination method coincide with each other. In other words, in the area R6, the normal ranges of the vital signs information used for the used determination method coincide with a vertical axis (an axis extending in an up-down direction in FIG. 5) in the area R6. The graphs G1 to G3 overlap with the area R61 or the area R63. Accordingly, the vital signs information overlaps with at least one of the normal range information or the abnormal range information. The color tone of the area R61 is different from color tones of the areas R62 and R63. That is, the color tone related to the display mode of the normal range information is different from the color tone related to the display mode of the abnormal range information. In the present embodiment, the color tone of the area R61 is gray, and the color tone of the areas R62 and R63 is black. That is, the color related to the display mode of the normal range information is lighter than the color related to the display mode of the abnormal range information. In other words, at least one of the brightness or the chroma related to the display mode of the normal range information is lower than at least one of the brightness or the chroma related to the display mode of the abnormal range information. The present specification is not intended to compare the brightness related to the display mode of the normal range information and the chroma related to the display mode of the abnormal range information, or the chroma related to the display mode of the normal range information and the brightness related to the display mode of the abnormal range information. For convenience of description, in FIG. 5, the presence or absence of dot hatching illustrates that the color tone related to the display mode of the normal range information is different from the color tone related to the display mode of the abnormal range information. This also applies to the display data illustrated in FIGS. 6 and 7.

The area R7 below the area R6 displays, among the vital signs information from 16:00, Dec. 10, 2022 to the current time, the vital signs information not used for the used determination method in a form of vital graphs extending on a timeline. Accordingly, the area R7 is an example of the second area. In the present embodiment, the vital signs information (the SpO2 information, the body temperature information, the heart rate information, and the oxygen support information) not used for qSOFA from 16:00, Dec. 10, 2022 to the current time is displayed in the area R7 in a form of vital graphs extending on the timeline. The vital graph indicating the SpO2 information is a graph G4. The vital graph indicating the body temperature information is a graph G5. The vital graph indicating the heart rate information is a graph G6. The vital graph indicating the oxygen support information is a graph G7. Timelines in the area R6 and the area R7 coincide with each other. That is, the timelines in the area R5, the area R6, and the area R7 all coincide with each other.

The area R7 can include an area R71 corresponding to the normal range of the vital signs information not used for the used determination method, and an area R72 and an area R73 corresponding to the abnormal ranges of the vital signs information not used for the used determination method. In the example illustrated in FIG. 5, the normal range and the abnormal range of the vital signs information not used for the used determination method are defined by a unified range U2 indicated by the unified range information generated by the controller 33 according to the above principle. Accordingly, in the area R7, a plurality of pieces of vital signs information (the graphs G4 to G7) are collectively displayed in the unified range U2. That is, in the area R7, display positions of the normal ranges of the vital signs information not used for the used determination method coincide with each other. In other words, in the area R7, the normal ranges of the vital signs information not used for the used determination method coincide with a vertical axis (an axis extending in the up-down direction in FIG. 5), in the area R7. The color tone of the area R71 is different from color tones of the areas R72 and R73. That is, the color tone related to the display mode of the normal range information is different from the color tone related to the display mode of the abnormal range information. In the present embodiment, the color tone of the area R71 is gray, and the color tone of the areas R72 and R73 is black. In the area R7, the same as or similar to the area R6, the presence or absence of dot hatching indicates that the color tone related to the display mode of the normal range information is different from the color tone related to the display mode of the abnormal range information.

In the areas R5, R6, and R7, a straight line L2 vertically crossing these areas is displayed. The straight line L2 indicates to which position of the timelines in the areas R5, R6, and R7 the specific time indicated by the selection time information (in the present embodiment, 17:52, Dec. 10, 2022) corresponds.

The area R8 below the area R7 displays the vital signs information (the respiratory information, the SpO2 information, the body temperature information, the blood pressure information, the heart rate information, the oxygen support information, and the consciousness information) of the subject at 17:52, Dec. 10, 2022. Accordingly, the area R8 is an example of the third area.

The area R9 on a left side of the area R8 displays, as the condition information of the used determination method at 17:52, Dec. 10, 2022, the score based on the used determination method. In the present embodiment, the used determination method is qSOFA, the score based on qSOFA at 17:52, Dec. 10, 2022 is 0, and thus "0" is displayed in the area R9.

The areas R3 and R5 are positioned above the areas R6 and R8. Accordingly, the score (an example of the condition information) displayed in the area R3 and the bar graphs (examples of the condition information) displayed in the area R5 are displayed above the graphs G1 to G7 (that is, the vital signs information used for the used determination method and the vital signs information not used for the determination method). The graphs G1 to G3 (that is, the vital signs information used for the used determination method) are displayed above the graphs G4 to G7 (that is, the vital signs information not used for the used determination method). In addition, the score displayed in the area R3 and the bar graphs displayed in the area R5 are displayed above a portion where the graphs G1 to G7 overlap with the background information in the area R6.

Next, display data displayed on the display 42, in a case where NEWS is used as the determination method will be described. For example, in a case where NEWS, which is the determination method indicated by the candidate determination method information, on the touch panel superimposed on the display 42 of the user terminal device 40 is tapped by the user, the display 42 displays a screen on which the display data illustrated in FIG. 6 is displayed. That is, in a case where the user operates the user terminal device 40 to switch the used determination method to the determination method selected by the user, the user terminal device 40 transmits a switching request signal to the display data generation apparatus 30. The display data generation apparatus 30 is configured to switch the used determination method to the selected determination method, based on the switching request signal. In this manner, in a case where the determination method indicated by the candidate determination method information is selected, the selected determination method indicated by the candidate determination method information (that is, NEWS) and the determination method indicated by the determination method information (that is, qSOFA) are switched. As illustrated in FIG. 6, contents displayed in the area R1 when NEWS is used are the same as the contents displayed in the area R1 when qSOFA is used.

Contents displayed in the area R2 when NEWS is used are similar to the contents displayed in the area R2 when qSOFA is used. However, in the example illustrated in FIG. 6, the straight line L1 is displayed below characters "NEWS".

Contents displayed in the area R3 when NEWS is used are similar to the contents displayed in the area R3 when qSOFA is used. However, in the example illustrated in FIG. 6, the used determination method is NEWS, a score based on NEWS at 18:30, Dec. 10, 2022 is 2, and thus "2" is displayed in the area R3.

Contents displayed in the area R4 when NEWS is used are the same as the contents displayed in the area R4 when qSOFA is used.

Contents displayed in the area R5 when NEWS is used are similar to the contents displayed in the area R5 when qSOFA is used. However, in the example illustrated in FIG. 6, scores based on NEWS in a period from 16:00, Dec. 10, 2022 to the current time are displayed in the area R5. In the present embodiment, when the score of NEWS is 1, a corresponding bar graph is colored in blue. When the score based on NEWS is 2, a corresponding bar graph is colored in green. When the score based on NEWS is 3 and there is no vital signs information having a score of 3 or more, a corresponding bar graph is colored in yellow. When the score based on NEWS is 4 and there is no vital signs information having a score of 3 or more, a corresponding bar graph is colored in orange. When the score based on NEWS is 5 or when there is one or more pieces of vital signs information having a score of 3 or more, a corresponding bar graph is colored in red. In FIG. 6, a bar graph hatched with oblique lines indicates a bar graph colored in blue. A bar graph hatched with vertical lines indicates a bar graph colored in green. A bar graph hatched with horizontal lines represents a bar graph colored in yellow.

Contents displayed in the area R6 when NEWS is used are similar to the contents displayed in the area R6 when qSOFA is used. However, in the example illustrated in FIG. 6, the vital signs information (the respiratory information, the SpO2 information, the body temperature information, the blood pressure information, the heart rate information, the oxygen support information, and the consciousness information) used for NEWS from 16:00, Dec. 10, 2022 to the current time is displayed in the area R6 in a form of vital graphs extending on the timeline. The vital graph indicating the respiratory information is a graph G11. The vital graph indicating the blood pressure information is a graph G12. The vital graph indicating the consciousness information is a graph G13. The vital graph indicating the SpO2 information is a graph G14. The vital graph indicating the body temperature information is a graph G15. The vital graph indicating the heart rate information is a graph G16. The vital graph indicating the oxygen support information is a graph G17. Also in the present embodiment, the color related to the display mode of the condition information is darker than the color related to the display mode of the background information. That is, at least one of the brightness or the chroma related to the display mode of the condition information is higher than at least one of the brightness or the chroma related to the display mode of the background information. The color related to the display mode of the background information is lighter than the colors related to the display modes of the graphs G11 to G17. That is, at least one of the brightness or the chroma related to the display mode of the background information is lower than at least one of the brightness or the chroma related to the display modes of the graphs G11 to G17.

Contents displayed in the area R7 when NEWS is used are similar to the contents displayed in the area R7 when qSOFA is used. However, since all the vital signs information (the respiratory information, the SpO2 information, the body temperature information, the blood pressure information, the heart rate information, the oxygen support information, and the consciousness information) input to the input interface 31 in the present embodiment is vital signs information used for NEWS, no vital signs information is displayed in the area R7 in the example illustrated in FIG. 6.

Contents displayed in the area R8 when NEWS is used are the same as the contents displayed in the area R8 when qSOFA is used.

Contents displayed in the area R9 when NEWS is used are similar to the contents displayed in the area R9 when qSOFA is used. However, in the example illustrated in FIG. 6, the used determination method is NEWS, a score based on NEWS at 17:52, Dec. 10, 2022 is 3, and thus "3" is displayed in the area R9.

As a method for determining a condition of a subject, for example, a determination method such as national early warning score (NEWS) is known. When the condition of the subject is determined by using such a determination method, condition information based on the determination method and vital signs information used for the used determination method may be displayed on a patient monitor or the like. However, when it is desired to evaluate the condition of the subject more comprehensively and/or more specifically, not only the vital signs information used for the used determination method may be confirmed, but also other vital signs information not used for the determination method may be confirmed. As described above, when the condition of the subject is determined by using the determination method such as NEWS, there is a need to confirm not only the vital signs information necessary for performing the determination method but also the vital signs information which is unnecessary.

The display data generation apparatus 30 having the above configuration generates display data, the display data including, among the input vital signs information, the vital signs information that is used for the determination method for determining the condition of the subject and is displayed in the area R6 (an example of the first area), and the vital signs information that is not used for the determination method and is displayed in the area R7 (an example of the second area). That is, the area in which the vital signs information used for the determination method is displayed is different from the area in which the vital signs information not used for the determination method is displayed. According to the display data generation apparatus 30, the vital signs information used for the determination method for determining the condition of the subject and the vital signs information not used for the determination method can be displayed separately. A display data generation method and a non-transitory computer-readable medium according to the above configuration can also implement the same or similar effect.

According to the display data generation apparatus 30 having the above configuration, in the areas R6 and R7, a plurality of pieces of vital signs information are collectively displayed in the unified range for uniformly defining the normal range and the abnormal range of the plurality of pieces of vital signs information. That is, in the areas R6 and R7, the plurality of pieces of vital signs information are collectively displayed in the unified range. Therefore, according to the display data generation apparatus 30, the user can easily visually recognize a plurality of pieces of vital signs information with a small amount of viewpoint movement, and thus a sense of burden on the user can be reduced.

According to the display data generation apparatus 30 having the above configuration, the vital signs information obtained at a specific time freely selected is displayed in the area R8 (an example of the third area). Therefore, the user can also confirm not only the vital graphs of the vital signs information extending on the timeline but also the vital signs information at a specific time by visually recognizing the vital signs information displayed in the area R8.

According to the display data generation apparatus 30 having the above configuration, all pieces of vital signs information obtained at the specific time are displayed in the area R8, and thus the user can comprehensively estimate the condition of the subject by visually recognizing the vital signs information displayed in the area R8.

According to the display data generation apparatus 30 having the above configuration, the display data includes the condition information indicating the condition of the subject, and thus the user can confirm not only the vital signs information used for the determination method and the vital signs information not used for the determination method but also the condition of the subject by using such display data. As a result, the user can comprehensively grasp the condition of the subject.

According to the display data generation apparatus 30 having the above configuration, the condition information is displayed above the vital signs information used for the determination method and the vital signs information not used for the determination method, and the vital signs information used for the determination method is displayed above the vital signs information not used for the determination method. Therefore, the user can confirm the condition information, the vital signs information used for the determination method, and the vital signs information not used for the determination method in this order, and thus can efficiently confirm the condition of the subject.

According to the display data generation apparatus 30 having the above configuration, the display data includes the determination method information indicating the used determination method, and the area R6 is configured to display the vital signs information that is used for the determination method indicated by the determination method information. The user can intuitively recognize the vital signs information used for the determination method by visually recognizing the determination method, and thus the user can easily and quickly recognize the vital signs information displayed in the first area by using such determination method information.

According to the display data generation apparatus 30 having the above configuration, the display data includes the candidate determination method information indicating the determination method that is selectable and is not used, and thus the user can easily recognize the selectable determination method by using the candidate determination method information.

According to the display data generation apparatus 30 having the above configuration, when the determination method indicated by the candidate determination method information is selected, the determination method indicated by the selected candidate determination method information and the determination method indicated by the determination method information are switched, and thus the switching of the determination method can be easily and quickly performed.

Second Embodiment

Figure 7:
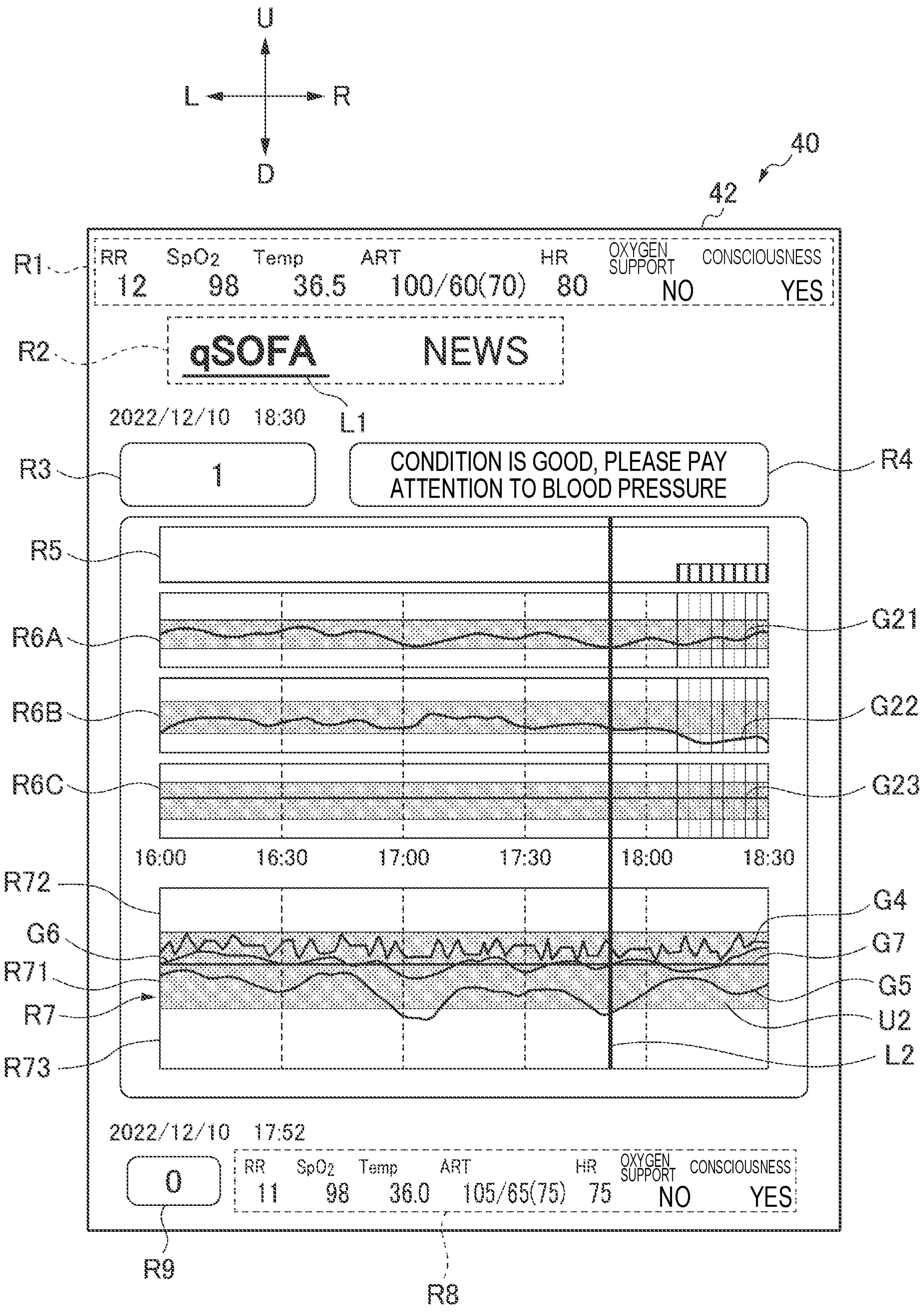
FIG. 7 illustrates an example of the screen on which display data is displayed.

Next, a display data generation method according to the present embodiment will be described with reference to FIGS. 4 and 7. In the present embodiment, the same or similar parts as those in the first embodiment are denoted by the same or similar reference numerals, and detailed description thereof will be appropriately omitted. Also in the present embodiment, the display data generation method illustrated in FIG. 4 is performed. Also in the present embodiment, a current time is assumed to be 18:30, Dec. 10, 2022. Further, also in the present embodiment, it is assumed that vital signs information is obtained from 16:00 to 18:30, Dec. 10, 2022.

STEP 01 to STEP 06 are the same as or similar to those in the first embodiment. In STEP 04, it is assumed that a user inputs determination method information indicating that the used determination method is qSOFA to the input 41 of the user terminal device 40.

The controller 33 generates unified range information for vital signs information (SpO2 information, body temperature information, heart rate information, and oxygen support information) not used for qSOFA (STEP 08). In the present embodiment, no unified range information is generated for vital signs information (respiratory information, blood pressure information, and consciousness information) used for qSOFA. A method for generating the unified range information in the present embodiment is the same as or similar to the method for generating the unified range information in the first embodiment, and a detailed description thereof will be omitted.

STEP 09 to STEP 14 are the same as or similar to those in the first embodiment. In STEP 10, it is assumed that the user inputs, to the input 41 of the user terminal device 40, selection time information indicating that a time at which the user desires to confirm the vital signs information is 17:52, Dec. 10, 2022.

Here, display data displayed on the display 42 of the user terminal device 40 in STEP 14 will be described. In the present embodiment, the display data displayed on the display 42 of the user terminal device 40 is display data illustrated in FIG. 7. Contents displayed in the areas R1 to R5 and the areas R7 to R9 in the present embodiment are the same as or similar to the contents displayed in the areas R1 to R5 and the areas R7 to R9 in the first embodiment. On the other hand, in the display data in the present embodiment, areas R6A to R6C are displayed instead of the area R6. The area R6A displays a vital graph G21 of the respiratory information. The area R6B displays a vital graph G22 of the blood pressure information. The area R6C displays a vital graph G23 of the consciousness information. The areas R6A, R6B, and R6C are examples of a first area. In this manner, the present embodiment is different from the first embodiment in that the vital signs information not used for the used determination method is collectively displayed in the unified range U2, and the vital signs information used for the used determination method is individually and separately displayed (that is, not collectively displayed in the unified range).

Also in the second embodiment, the display data generation apparatus 30 can implement the same or similar effects as those of the first embodiment.

According to the display data generation apparatus 30 having the above configuration, in the area R7 (an example of a second area), a plurality of pieces of the vital signs information is collectively displayed in the unified range U2. The vital signs information not used for the determination method for determining a condition of a subject has a priority to be confirmed lower than that of the vital signs information used for the determination method. According to the display data generation apparatus 30, the vital signs information displayed in the area R7 is vital signs information not used for the determination method for determining the condition of the subject, and thus the user can efficiently visually recognize the vital signs information.

The above-described embodiments are for facilitating understanding of the presently disclosed subject matter, and do not limit the presently disclosed subject matter. The presently disclosed subject matter can be modified or improved without departing from the gist thereof.

Figure 8:
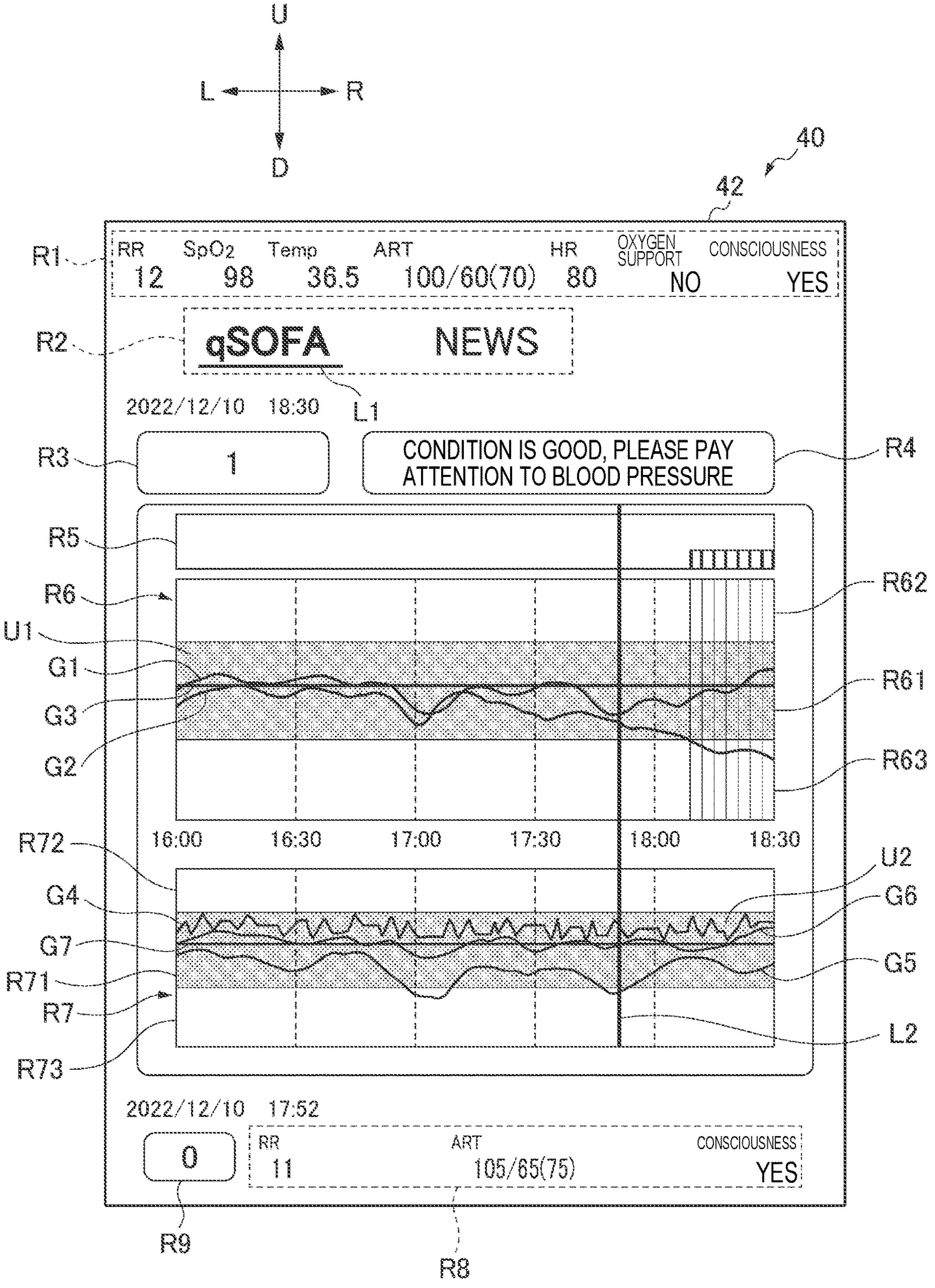
FIG. 8 illustrates an example of the screen on which display data is displayed.

In the above embodiments, the area R8 (an example of a third area) displays the respiratory information, the SpO2 information, the body temperature information, the blood pressure information, the heart rate information, the oxygen support information, and the consciousness information obtained at 17:52, Dec. 10, 2022 (an example of a specific time freely selected by the user), and the presently disclosed subject matter is not limited to this example. For example, the area R8 may display only the vital signs information used for the used determination method among the vital signs information obtained at the specific time freely selected by the user. For example, when the used determination method is qSOFA, the display data displayed on the display 42 of the user terminal device 40 is display data illustrated in FIG. 8. The display data illustrated in FIG. 8 is different from the display data illustrated in FIG. 5 in that only the respiratory information, the blood pressure information, and the consciousness information, which are vital signs information used for qSOFA, are displayed in the area R8. When the display data generation apparatus 30 generates the display data illustrated in FIG. 8, only the vital signs information used for the determination method for determining the condition of the subject among the vital signs information obtained at the specific time is displayed in the area R8. For this reason, the user can quickly recognize the vital signs information used for the determination method by visually recognizing the vital signs information displayed in the area R8.

In the above embodiments, the display data is displayed on the display 42 of the user terminal device 40, and may be displayed on the display 34 of the display data generation apparatus 30 or the display 24 of the bedside monitor 20, for example.

In the above embodiments, the display data can include the vital signs information, the background information, the normal range information, the abnormal range information, the condition information, the determination method information, the candidate determination method information, and the identification information, but the presently disclosed subject matter is not limited these examples. For example, the display data may not include the background information, the normal range information, the abnormal range information, the condition information, the determination method information, the candidate determination method information, or the identification information.

In the above embodiments, a plurality of pieces of vital signs information are input to the input interface 31, but one piece of vital signs information may be input.

In the second embodiment, the vital signs information used for the used determination method is individually and separately displayed, and the vital signs information not used for the determination method is collectively displayed in the unified range U2, but the presently disclosed subject matter is not limited to this example. For example, all the obtained vital signs information (that is, the vital signs information used for the used determination method and the vital signs information not used for the determination method) may be displayed in individually separated areas. In addition, for example, the vital signs information used for the used determination method may be collectively displayed in the unified range U1, and the vital signs information not used for the determination method may be displayed in individually separated areas.

In the above embodiments, the respiratory information, the SpO2 information, the body temperature information, the blood pressure information, the heart rate information, the oxygen support information, and the consciousness information are input to the input interface 31, but only the vital signs information used for the determination method may be input, for example.

In the first embodiment, for example, when the used determination method is qSOFA, three pieces of vital signs information are displayed in the unified range U1 of the area R6, and four pieces of vital signs information are displayed in the unified range U2 of the area R7, but the presently disclosed subject matter is not limited thereto, and the number of pieces of vital signs information displayed in the unified ranges U1 and U2 may be two or more.

In the above embodiments, two determination methods (qSOFA and NEWS) are displayed in the area R2, but three or more determination methods may be displayed, for example.

In the above embodiments, the display data generation system 1 can include the sensor 10, the bedside monitor 20, the display data generation apparatus 30, and the user terminal device 40, but the display data generation system 1 may not include the display data generation apparatus 30 or the user terminal device 40. In this case, the bedside monitor 20 may include a storage and the controller 22 corresponding to the storage 32 and the controller 33 of the display data generation apparatus 30, and the bedside monitor 20 may implement functions of the display data generation apparatus 30. The display data generation system 1 may not include the bedside monitor 20 or the display data generation apparatus 30. In this case, the user terminal device 40 may include a storage and a controller corresponding to the storage 32 and the controller 33 of the display data generation apparatus 30, and the user terminal device 40 may implement functions of the display data generation apparatus 30.

In the above embodiments, the display data is generated by the display data generation apparatus 30, and may also be generated by the bedside monitor 20 or the user terminal device 40. In this case, the bedside monitor 20 or the user terminal device 40 can include, for example, a controller corresponding to the display data generation apparatus 30, and obtains various types of information from the storage 32 of the display data generation apparatus 30.

As described above, the following matters are disclosed in the present specification.

(1) A display data generation apparatus including:

an input interface configured to receive vital signs information on a subject;

one or more processors; and one or more memories configured to store at least one instruction to be executed by the processor, in which, in a case where the at least one instruction is executed by the processor, the display data generation apparatus generates display data, and in which the display data includes, among the vital signs information received by the input interface:

a first vital signs information that is used in a determination method for determining a condition of the subject, the first vital signs information being displayed in a first area; and a second vital signs information that is not used in the determination method, the second vital signs information being displayed in a second area different from the first area.

(2) The display data generation apparatus according to (1), in which the display data further includes:

normal range information indicating a normal range of the vital signs information set for each piece of the vital signs information; and abnormal range information indicating an abnormal range of the vital signs information set for each piece of the vital signs information, at least one of the first area or the second area includes a unified range, the unified range being based on the normal range information and the abnormal range information corresponding to each piece of the vital signs information, the unified range being for uniformly defining the normal range and the abnormal range of a plurality of pieces of the vital signs information received by the input interface, and at least two pieces of the vital signs information are collectively displayed in the unified range in at least one of the first area or the second area.

(3) The display data generation apparatus according to (2), in which at least two pieces of the vital signs information are collectively displayed in the unified range in the second area.

(4) The display data generation apparatus according to any one of (1) to (3), in which the display data includes a third area different from the first area and the second area, at least one of the first area or the second area is configured to display a vital graph of the vital signs information, the vital graph extending on a timeline, and the third area is configured to display vital signs information obtained at a specific time selected freely, among the vital signs information displayed in the first area and the second area.

(5) The display data generation apparatus according to (4), in which the third area is configured to display all pieces of the vital signs information obtained at the specific time.

(6) The display data generation apparatus according to (4), in which the third area is configured to display only the vital signs information used in the determination method, among the vital signs information obtained at the specific time.

(7) The display data generation apparatus according to any one of (1) to (6), in which the display data further includes condition information, that the condition information indicating a condition of the subject, the condition information being generated based on the first vital signs information used in the determination method and the determination method.

(8) The display data generation apparatus according to (7), in which the condition information is displayed above the first vital signs information used in the determination method and the second vital signs information not used in the determination method, and the first vital signs information used in the determination method is displayed above the second vital signs information not used in the determination method.

(9) The display data generation apparatus according to any one of (1) to (8), in which the display data further includes determination method information indicating the determination method to be used, and the first area is configured to display vital signs information that is used in the determination method indicated by the determination method information.

(10) The display data generation apparatus according to (9), in which the display data includes candidate determination method information indicating the determination method that is selectable and is not used.

(11) The display data generation apparatus according to (10), in which in a case where the determination method indicated by the candidate determination method information is selected, the selected determination method indicated by the candidate determination method information, and the determination method indicated by the determination method information are switched.

(12) A display data generation method executed by a display data generation apparatus, the display data generation method including:

generating display data, the display data including, among vital signs information on a subject:

a first vital signs information that is used in a determination method for determining a condition of the subject, the first vital signs information being displayed in a first area; and a second vital signs information that is not used for the determination method, the second vital signs information being displayed in a second area different from the first area.

(13) A non-transitory computer readable storage medium storing a computer program including instructions which, when executed by one or more processors provided in a display data generation apparatus, cause the display data generation apparatus to:

generate display data, the display data including, among vital signs information on a subject:

a first vital signs information that is used for a determination method for determining a condition of the subject, the first vital signs information being displayed in a first area; and a second vital signs information that is not used for the determination method, the second vital signs information being displayed in a second area different from the first area.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A display data generation apparatus comprising:

an input interface configured to receive vital signs information on a subject;

one or more processors; and one or more memories configured to store at least one instruction to be executed by the processor, wherein, in a case where the at least one instruction is executed by the processor, the display data generation apparatus generates display data, and wherein the display data includes, among the vital signs information received by the input interface:

a first vital signs information that is used in a determination method for determining a condition of the subject, the first vital signs information being collectively displayed in a first area; and a second vital signs information that is not used in the determination method, the second vital signs information being collectively displayed in a second area different from the first area, wherein the first area and the second area are simultaneously displayed, and wherein the display data further includes:

normal range information indicating a normal range of the vital signs information set for each piece of the vital signs information; and abnormal range information indicating an abnormal range of the vital signs information set for each piece of the vital signs information, at least one of the first area or the second area includes a unified range, the unified range being based on the normal range information and the abnormal range information corresponding to each piece of the vital signs information, the unified range being for uniformly defining the normal range and the abnormal range of a plurality of pieces of the vital signs information received by the input interface, and at least two pieces of the vital signs information are collectively displayed in the unified range in at least one of the first area or the second area.

2. The display data generation apparatus according to claim 1, wherein at least two pieces of the vital signs information are collectively displayed in the unified range in the second area.

3. The display data generation apparatus according to claim 1, wherein the display data includes a third area different from the first area and the second area, at least one of the first area or the second area is configured to display a vital graph of the vital signs information, the vital graph extending on a timeline, and the third area is configured to display vital signs information obtained at a specific time selected freely, among the vital signs information displayed in the first area and the second area.

4. The display data generation apparatus according to claim 3, wherein the third area is configured to display all pieces of the vital signs information obtained at the specific time.

5. The display data generation apparatus according to claim 1, wherein the display data further includes condition information, that the condition information indicating a condition of the subject, the condition information being generated based on the first vital signs information used in the determination method.

6. The display data generation apparatus according to claim 5, wherein the condition information is displayed above the first vital signs information used in the determination method and the second vital signs information not used in the determination method, and the first vital signs information used in the determination method is displayed above the second vital signs information not used in the determination method.

7. The display data generation apparatus according to claim 1, wherein the display data further includes determination method information indicating the determination method to be used, and the first area is configured to display vital signs information that is used in the determination method indicated by the determination method information.

8. The display data generation apparatus according to claim 1, wherein the display data further includes an axis that overlaps with the unified range in the at least one of the first area of the second area including the unified range.

9. A display data generation apparatus comprising:

an input interface configured to receive vital signs information on a subject;

one or more processors; and one or more memories configured to store at least one instruction to be executed by the processor, wherein, in a case where the at least one instruction is executed by the processor, the display data generation apparatus generates display data, wherein the display data includes, among the vital signs information received by the input interface:

a first vital signs information that is used in a determination method for determining a condition of the subject, the first vital signs information being collectively displayed in a first area; and a second vital signs information that is not used in the determination method, the second vital signs information being collectively displayed in a second area different from the first area, wherein the first area and the second area are simultaneously displayed, wherein the display data includes a third area different from the first area and the second area, at least one of the first area or the second area is configured to display a vital graph of the vital signs information, the vital graph extending on a timeline, and the third area is configured to display vital signs information obtained at a specific time selected freely, among the vital signs information displayed in the first area and the second area, wherein the third area is configured to display only the vital signs information used in the determination method, among the vital signs information obtained at the specific time.

10. A display data generation apparatus comprising:

an input interface configured to receive vital signs information on a subject;

one or more processors; and one or more memories configured to store at least one instruction to be executed by the processor, wherein, in a case where the at least one instruction is executed by the processor, the display data generation apparatus generates display data, wherein the display data includes, among the vital signs information received by the input interface:

a first vital signs information that is used in a determination method for determining a condition of the subject, the first vital signs information being displayed in a first area; and a second vital signs information that is not used in the determination method, the second vital signs information being displayed in a second area different from the first area, wherein the display data further includes determination method information indicating the determination method to be used, the first area is configured to display vital signs information that is used in the determination method indicated by the determination method information, and wherein the display data includes candidate determination method information indicating the determination method that is selectable and is not used.

11. The display data generation apparatus according to claim 10, wherein in a case where the determination method indicated by the candidate determination method information is selected, the selected determination method indicated by the candidate determination method information, and the determination method indicated by the determination method information are switched.

12. A display data generation method executed by a display data generation apparatus, the display data generation method including:

generating display data, the display data including, among vital signs information on a subject:

a first vital signs information that is used in a determination method for determining a condition of the subject, the first vital signs information being collectively displayed in a first area;

a second vital signs information that is not used for the determination method, the second vital signs information being collectively displayed in a second area different from the first area, wherein the first area and the second area are simultaneously displayed;

normal range information indicating a normal range of the vital signs information set for each piece of the vital signs information; and abnormal range information indicating an abnormal range of the vital signs information set for each piece of the vital signs information, at least one of the first area or the second area includes a unified range, the unified range being based on the normal range information and the abnormal range information corresponding to each piece of the vital signs information, the unified range being for uniformly defining the normal range and the abnormal range of a plurality of pieces of the vital signs information received by the input interface, and at least two pieces of the vital signs information are collectively displayed in the unified range in at least one of the first area or the second area.

13. A non-transitory computer readable storage medium storing a computer program comprising instructions which, when executed by one or more processors provided in a display data generation apparatus, cause the display data generation apparatus to:

generate display data, the display data including, among vital signs information on a subject:

a first vital signs information that is used for a determination method for determining a condition of the subject, the first vital signs information being collectively displayed in a first area;

a second vital signs information that is not used for the determination method, the second vital signs information being collectively displayed in a second area different from the first area, wherein the first area and the second area are simultaneously displayed;

normal range information indicating a normal range of the vital signs information set for each piece of the vital signs information; and abnormal range information indicating an abnormal range of the vital signs information set for each piece of the vital signs information, at least one of the first area or the second area includes a unified range, the unified range being based on the normal range information and the abnormal range information corresponding to each piece of the vital signs information, the unified range being for uniformly defining the normal range and the abnormal range of a plurality of pieces of the vital signs information received by the input interface, and at least two pieces of the vital signs information are collectively displayed in the unified range in at least one of the first area or the second area.

* * * * *